United States Patent [19]

Caton et al.

[11] 3,933,890
[45] Jan. 20, 1976

[54] 10,11,15-TRIHYDROXYPROSTANOIC ACID

[75] Inventors: Michael Peter Lear Caton, Upminster; Trevor Parker, Romford, both of England

[73] Assignee: May & Baker Limited, England

[22] Filed: Dec. 7, 1973

[21] Appl. No.: 423,376

Related U.S. Application Data

[62] Division of Ser. No. 332,660, Feb. 15, 1973.

[30] Foreign Application Priority Data

Feb. 18, 1972  United Kingdom............... 7640/72

[52] U.S. Cl... 260/468 D; 260/247.2 R; 260/268 R; 260/293.6 S; 260/321.2; 260/501.1; 260/501.17; 260/514 D
[51] Int. Cl.[2].................. C07C 61/38; C07C 69/74
[58] Field of Search...................... 260/468 D, 514 D

[56] References Cited
UNITED STATES PATENTS
3,846,475  11/1974  Crabbe et al. ................... 260/468

OTHER PUBLICATIONS
Crabbe et al., J. C. S. 119 (1973).

*Primary Examiner*—Robert Gerstl
*Attorney, Agent, or Firm*—Stevens, Davis, Miller & Mosher

[57] ABSTRACT

Cyclopentane derivatives of the formula:

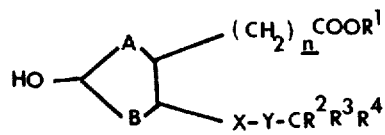

(wherein the R symbols represent hydrogen or alkyl, n represents 4 or 6, and the symbols A, B, X and Y have any one of the following combinations: (a) A represents methylene, B represents hydroxymethylene, X represents ethylene and Y represents hydroxymethylene; (b) A represents carbonyl, B represents methylene, X represents ethylene or trans-vinylene and Y represents hydroxymethylene or carbonyl; or (c) A represents hydroxymethylene, B represents methylene, X represents ethylene or trans-vinylene and Y represents hydroxymethylene) are new compounds, possessing pharmacological properties, in particular, the production of hypotension, bronchodilatation, inhibition of gastric acid secretion and stimulation of uterine contraction.

10 Claims, No Drawings

10,11,15-TRIHYDROXYPROSTANOIC ACID

This is a division of application Ser. No. 332,660, filed Feb. 15, 1973.

This invention relates to new cyclopentane derivatives, a process for their preparation, certain intermediates used in their preparation, and compositions containing the new cyclopentane derivatives.

According to the present invention, there are provided the new cyclopentane derivatives of the general formula:

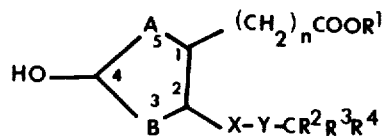

[wherein $R^1$ represents a hydrogen atom or a straight- or branched-chain alkyl group containing from 1 to 12 (for example from 1 to 4 or from 7 to 12) carbon atoms, $R^2$ and $R^3$ are identical or different and each represents a hydrogen atom or a straight- or branched-chain alkyl group containing from 1 to 4 carbon atoms, for example a methyl group, $R^4$ represents a hydrogen atom or, preferably, a straight- or branched-chain alkyl group containing from 1 to 10 (preferably from 2 to 9, for example 3, 4 or 6) carbon atoms, n represents 4 or, preferably, 6, and the symbols A, B, X and Y have any one of the following combinations: (a) A represents a methylene group, B represents a hydroxymethylene group, X represents an ethylene group and Y represents a hydroxymethylene group, (b) A represents a carbonyl group, B represents a methylene group, X represents an ethylene or trans-vinylene group and Y represents a hydroxymethylene group or carbonyl group; or (c) A represents a hydroxymethylene group, B represents a methylene group, X represents an ethylene or trans-vinylene group and Y represents a hydroxymethylene group] and, when $R^1$ represents a hydrogen atom, non-toxic salts thereof.

As will be apparent to those skilled in the art, the structure shown in general formula I has at least three centres of chirality, these three centres of chirality being at the ring carbon atoms in positions 1, 2 and 4 respectively. In addition to these three centres of chirality, further centres of chirality occur when A, B or Y represents a hydroxymethylene group, at the carbon atoms in those hydroxymethylene groups, and still further centres of chirality may occur in the group $-CR^2R^3R^4$ or in alkyl groups represented by the groups $R^1$, $R^2$, $R^3$ and $R^4$. The presence of centres of chirality, as is well known, leads to the existence of isomerism. However, the compounds of formula I of the present invention all have such a configuration that the side chains attached to the ring carbon atoms in positions 1 and 2 are trans with respect to each other. Accordingly, all isomers of general formula I, and mixtures thereof, which have those side chains, attached to the ring carbon atoms in positions 1 and 2, in the trans configuration are within the scope of the present invention.

The compounds of formula I and, when $R^1$ represents a hydrogen atom, non-toxic salts thereof, possess valuable pharmacological properties including, in particular, the production of hypotension, bronchodilatation, inhibition of gastric acid secretion, and stimulation of uterine contraction. In laboratory screening tests the compounds produce:

a. a 10mmHg fall in the mean blood pressure of the urethane-anaesthetised, pempidine-treated normotensive rat at doses between 0.0005 and 2.0mg/kg animal body weight administered intravenously;

b. a 50% inhibition of the bronchoconstriction induced by administration of a bronchoconstrictor agonist, e.g. histamine or 5-hydroxytryptamine, in the urethane-anaesthetised guinea-pig when administered intravenously at doses between 0.005 and 100 μg/kg animal body weight;

c. a 50% inhibition of pentagastrin-induced gastric acid secretion in the rat at doses of between 1.0 and 100 μg/kg animal body weight/minute when administered orally in solution in an aqueous sodium chloride solution;

d. a 100% increase in amplitude of contraction of the uterus of the pregnant rat when administered intravenously at doses between 0.1 and 10mg/kg body weight.

According to a feature of the present invention the compounds of formula I are prepared by a process involving, as the final stage, a procedure of esterification, hydrolysis or reduction. Thus:

1. Compounds of formula I wherein $R^1$ represents an alkyl group are prepared by the esterification of corresponding compounds of formula I wherein $R^1$ represents a hydrogen atom. The esterification can be carried out by reaction with an alcohol of the general formula:

$$R^5OH \qquad \text{II}$$

(wherein $R^5$ represents a straight- or branched-chain alkyl group containing from 1 to 12 carbon atoms), an excess of which may be employed as solvent medium, in the presence of an inorganic acid, e.g. hydrochloric acid or sulphuric acid, preferably at a temperature between 50°C. and 160°C., and advantageously at the reflux temperature of the reaction mixture, or, when $R^5$ can be represented by the formula $-CHR^6R^7$ (wherein the symbols $R^6$ and $R^7$ are identical or different and each represents an alkyl group, the total number of carbon atoms in the two alkyl groups being at most 11, or, preferably, a hydrogen atom), by reaction with a diazoalkane of the general formula:

$$R^6R^7C=N_2 \qquad \text{III}$$

(wherein $R^6$ and $R^7$ are as hereinbefore defined) in an inert organic solvent medium, preferably a dialkyl ether (e.g. diethyl ether) preferably at ambient temperature.

Alternatively, a silver salt of such carboxylic acids of formula I can be reacted with an alkyl halide of the general formula:

$$R^5Z^1 \qquad \text{IV}$$

(wherein $Z^1$ represents a halogen atom and $R^5$ is as hereinbefore defined), optionally in the presence of an inert organic solvent, for example an aromatic hydrocarbon (e.g. benzene), at elevated temperature, for example at between 40° and 110°C., and advantageously at the reflux temperature of the reaction mixture.

2a. Compounds of formula I wherein $R^1$ represents a hydrogen atom, and especially those wherein A or B represents a hydroxymethylene group and those wherein X represents an ethylene group, the various other symbols being as hereinbefore defined, are prepared by the hydrolysis, preferably the alkaline hydrolysis, of corresponding compounds of formula I wherein $R^1$ represents an alkyl group $R^5$. The hydrolysis is preferably effected by treatment with an alkali metal hydroxide, for example sodium hydroxide, in an aqueous organic solvent medium, for example aqueous ethanol, optionally at an elevated temperature, for example between 40° and 110°C., e.g., at the reflux temperature of the reaction mixture.

2b. Compounds of formula I wherein B represents a methylene group and A and Y are identical, each representing either carbonyl or hydroxymethylene groups ($R^1$, $R^2$, $R^3$, $R^4$, $n$ and X being as hereinbefore defined), are prepared by the acid hydrolysis of compounds of general formula V or, when A represents a carbonyl group and Y represents a hydroxymethylene group, by the acid hydrolysis of compounds of general formula VI:

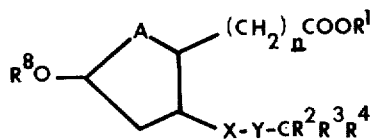

V $$R^9O \quad OR^9$$

(CH$_2$)$_n$COOR$^1$

HO

X-CH-CR$^2$R$^3$R$^4$
|
OH

VI (wherein $R^1$, $R^2$, $R^3$, $R^4$, $n$ and X are as hereinbefore defined, A and Y both represent carbonyl groups or hydroxymethylene groups, $R^8$ represents a 2-tetrahydropyranyl group unsubstituted or substituted by, for example, at least one alkyl group, and the symbols $R^9$ represent identical alkyl groups or together form an ethylene linkage unsubstituted or substituted by identical alkyl groups on each carbon atom, the symbols $R^9$ preferably representing together an unsubstituted ethylene linkage).

Hydrolysis of compounds of formula V is generally effected by treatment with an aqueous inorganic acid, e.g. dilute hydrochloric acid or a catalytic quantity of perchloric acid, or an aqueous organic acid, for example aqueous acetic acid, e.g. 50–80% v/v aqueous acetic acid, preferably in the presence of an inert organic solvent, for example a lower alkanol, e.g. ethanol, and optionally in the presence of a cation exchange resin, e.g. Dowex AG50W-X8 H$^+$ resin. The hydrolysis is generally carried out at temperatures between 0° and 100°C.; when dilute hydrochloric acid is used, at between 40° and 80°C., preferably between 50° and 60°C.; when a catalytic quantity of perchloric acid is used, at between 0°C. and 40°C., preferably between 15° and 25°C.; and when aqueous acetic acid is used, at between 0° and 80°C., preferably between 35° and 45°C.

Hydrolysis of compounds of formula VI is generally effected with an aqueous organic acid, for example aqueous acetic acid, e.g. 80% v/v aqueous acetic acid, preferably at temperatures between 5° and 100°C., more particularly between 15° and 30°C.

2c. Compounds of formula I wherein A represents a methylene group, B and Y represent hydroxymethylene groups and X represents an ethylene group ($R^1$, $R^2$, $R^3$, $R^4$ and $n$ being as hereinbefore defined) are prepared by the acid hydrolysis of compounds of the general formula:

$$R^8O \underset{OR^8 \quad OR^8}{\diagdown} \overset{(CH_2)_n COOR^1}{\diagup} CR^2R^3R^4$$

VII wherein $R^1$, $R^2$, $R^3$, $R^4$, $R^8$ and $n$ are as hereinbefore defined. The hydrolysis is generally carried out in conditions similar to those hereinbefore described for the acid hydrolysis of compounds of formula V.

3. Compounds of formula I wherein B represents a methylene group ($R^1$, $R^2$, $R^3$, $R^4$, A, X, Y and $n$ being as hereinbefore defined), but wherein X and Y do not simultaneously represent a vinylene group and a carbonyl group respectively (hereinafter referred to as "compounds of formula Ia"), are prepared by the reduction of compounds of formula I wherein B represents a methylene group (wherein $R^1$, $R^2$, $R^3$, $R^4$, $n$ and Y are as hereinbefore defined), but wherein X and A do not simultaneously represent an ethylene group and a hydroxymethylene group respectively (hereinafter referred to as "compounds of formula Ib"). Thus:

3a. Compounds of formula Ia wherein X represents an ethylene or vinylene group and A and Y represent hydroxymethylene groups are prepared by reduction of the corresponding compounds of formula Ib wherein X represents an ethylene or vinylene group, A represents a carbonyl group and Y represents a carbonyl or hydroxymethylene group, using means and conditions capable of reducing carbonyl groups to hydroxymethylene groups without affecting carbon-carbon double bonds. The reduction is preferably effected by a metal borohydride (e.g., sodium borohydride or potassium borohydride), usually in an aqueous, alcoholic or aqueous alcoholic medium and at between −40° and +30°C., preferably between −5°and +15°C., optionally in the presence of a base, for example an alkali metal hydroxide (e.g., aqueous sodium hydroxide or aqueous potassium hydroxide) or, especially when potassium borohydride is employed, in aqueous or aqueous alcoholic conditions buffered at a pH of from pH7 to pH9, e.g. at pH8 (e.g. by the addition of aqueous citric acid solution). Alternatively the reduction is carried out by reaction with aluminium isopropoxide, in the presence of isopropanol, preferably as the solvent medium, at an elevated temperature, advantageously at the reflux temperature of the reaction mixture.

3b. Compounds of formula Ia wherein X represents an ethylene group, A represents a carbonyl group and Y represents a carbonyl or hydroxymethylene group, are prepared by reduction of the corresponding compounds of formula Ib wherein X represents a vinylene group, A represents a carbonyl group and Y represents a carbonyl or hydroxymethylene group, with means and in conditions capable of reducing carbon-carbon double bonds without affecting carbonyl groups. The reduction is preferably effected by hydrogenation in the presence of a hydrogenation catalyst, for example rhodium on charcoal, in the presence of an inert organic solvent, for example a lower alkanol, e.g., ethanol, generally at ambient temperature and elevated pressure, e.g., at a hydrogen pressure of 15 kilograms per square centimeter.

3c. Compounds of formula Ia wherein X represents an ethylene group and A and Y represent hydroxymethylene groups, are prepared by reduction of corresponding compounds of formula Ib with means and in conditions capable of reducing any carbonyl groups present to hydroxymethylene groups and any vinylene groups present to ethylene groups. The reduction is preferably effected by hydrogenation in the presence of a hydrogenation catalyst, for example palladium on charcoal, in the presence of an inert organic solvent, for example a lower alkanol, e.g., ethanol, preferably at an elevated pressure, e.g., at a hydrogen pressure of 15 kilograms per square centimeter.

Compounds of formulae V, VI and VII are prepared, by the application of certain multi-stage procedures described hereinafter, from compounds of the general formula:

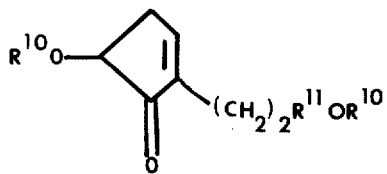
VIII

[wherein both symbols $R^{10}$ represent hydrogen atoms or identical alkanoyl groups containing from 1 to 5 carbon atoms, preferably acetyl, and $R^{11}$ represents a divalent group of the general formula IX or X:

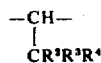
IX

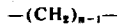
X $R^2$, $R^3$, $R^4$ and $n$ being as hereinbefore defined. Preferably the symbols $R^{10}$ represent hydrogen atoms when $R^{11}$ represents a group of formula X wherein $n$ represents 6, and preferably the symbols $R^{10}$ represent alkanoyl groups when $R^{11}$ represents a group of formula IX (wherein $R^2$, $R^3$ and $R^4$ are as hereinbefore defined) or a group of formula X wherein $n$ represents 4].

The compounds of formula VIII are novel compounds and important intermediates and they and the hereinafter described process for their preparation are features of the present invention.

Thus, as a feature of the present invention, compounds of formula VIII are prepared by the reaction of a compound of the general formula:

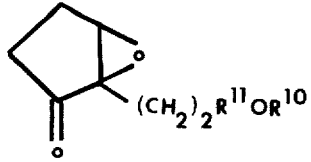
XI (wherein $R^{10}$ and $R^{11}$ are as hereinbefore defined) with an acid, preferably as the reaction medium and preferably at an elevated temperature, for example the reflux temperature of the reaction mixture. For the preparation of compounds of formula VIII wherein $R^{10}$ represents an alkanoyl group, the acid reagent used is the corresponding alkanoic acid of formula $R^{10}OH$; and for the preparation of compounds of formula VIII wherein $R^{10}$ represents a hydrogen atom, the acid reagent used is a mineral acid, preferably a dilute mineral acid, for example dilute sulphuric acid, preferably in the presence of an inert organic solvent, e.g., acetone or dioxan.

Compounds of formula XI are prepared by the epoxidation of compounds of the general formula:

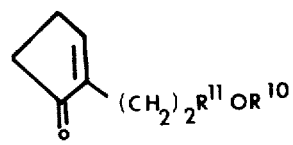
XII (wherein $R^{10}$ and $R^{11}$ are as hereinbefore defined), preferably by reaction with hydrogen peroxide and an alkali metal hydroxide (for example sodium hydroxide) in an inert organic solvent, for example a lower alkanol (e.g. methanol) at a temperature near or below the ambient temperature, preferably at 0°–25°C., advantageously at 10°–15°C.

Compounds of formula XII wherein $R^{11}$ represents a group of formula IX and $R^{10}$ represents a hydrogen atom are prepared by the hydrolysis, preferably the alkaline hydrolysis, of corresponding compounds of formula XII wherein $R^{11}$ represents a group of formula IX and $R^{10}$ represents an alkanoyl group. The hydrolysis may be effected, for example, by the action of an aqueous solution of an alkali metal carbonate, e.g., sodium carbonate, preferably in the presence of an inert organic solvent, for example an alcohol, e.g., ethanol.

Compounds of formula XII wherein $R^{11}$ represents a group of formula IX and $R^{10}$ represents an alkanoyl group may be prepared by the reaction of compounds of the general formula:

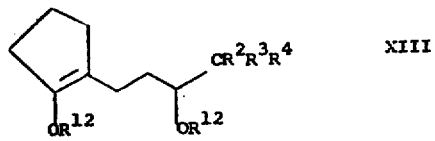
XIII (wherein $R^2$, $R^3$ and $R^4$ are as hereinbefore defined and $R^{12}$ represents an alkanoyl group containing from 1 to 5 carbon atoms) with a halogen, preferably bromine, in an inert organic solvent, for example a halogenated hydrocarbon (e.g. carbon tetrachloride), preferably at a temperature between 0° and −10°C., followed by treatment with a base, for example (a) a tertiary amine, e.g., triethylamine, preferably in the presence of an inert organic solvent, for example a halogenated hydrocarbon (e.g., carbon tetrachloride), and preferably at an elevated temperature, advantageously at the reflux temperature of the reaction mixture, or (b) an aqueous inorganic base, for example an alkali metal carbonate, e.g., sodium carbonate, preferably at room temperature.

Compounds of formula XII wherein $R^{11}$ represents a group of formula X and $R^{10}$ represents an alkanoyl group may be prepared by the acylation of the corresponding compound of formula XII wherein $R^{11}$ represents a group of formula X and $R^{10}$ represents a hydrogen atom with an appropriate acylating agent, for example with an acid anhydride of formula $(R^{13}CO)_2O$ [wherein $R^{13}$ represents an alkyl group containing from 1 to 4 carbon atoms] or, where $R^{10}$ represents a formyl group, with formic acid. Preferably the acylation is effected at an elevated temperature, e.g. at temperatures up to 100°C.

Compounds of formula XII wherein $R^{11}$ represents a group of formula X and $R^{10}$ represents a hydrogen atom may be prepared by the reaction of an enamine of the general formula:

XIV (wherein $R^{14}$ and $R^{15}$ each represents an alkyl group or together $R^{14}$ and $R^{15}$ represent a 4- or 5-membered hydrocarbon chain, which may be interrupted by one or two oxygen or nitrogen atoms — where such additional nitrogen atoms are of the form —N= or

where $R^{16}$ represents an alkyl group — the carbon atoms in the said hydrocarbon chain optionally each carrying 1 or 2 alkyl groups) with an aldehyde of the general formula:

$$R^{17}O(CH_2)_nCHO \quad XV$$

(wherein $R^{17}$ represents a hydrogen atom or a group $R^8$ as hereinbefore defined and $n$ is as hereinbefore defined). The reaction is carried out by heating in an inert organic solvent, for example an aromatic hydrocarbon (e.g. benzene) with continuous removal of water, preferably at 60°–120°C., followed by hydrolysis in aqueous acid conditions (e.g. with hydrochloric acid) preferably at ambient temperature, and then heating with an acid (e.g. concentrated hydrochloric acid), preferably at about 100°C., and preferably in an inert organic solvent such as an alcohol (e.g. butanol), to cause the double bond to migrate from the exocyclic to the endocyclic position.

Compounds of formula XIII may be prepared by the application of the following reaction scheme:

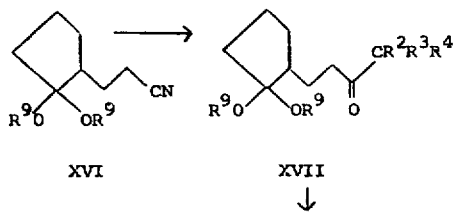

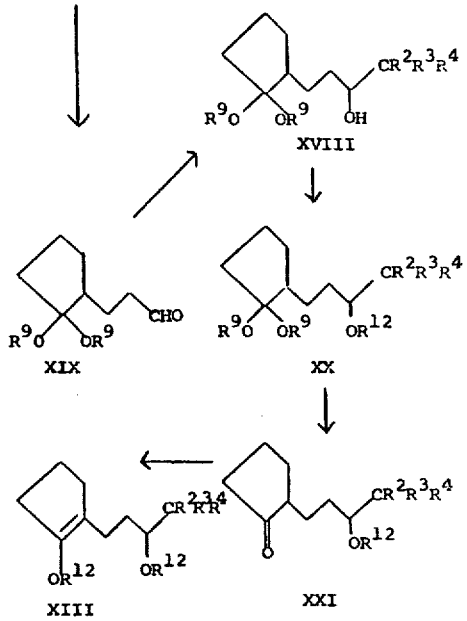

wherein $R^2$, $R^3$, $R^4$, $R^9$ and $R^{12}$ are as hereinbefore defined.

Thus, compounds of formula XVII are prepared by the reaction of compounds of formula XVI [which may be prepared by the application or adaptation of known methods, for example as described by T. Henshall and E. W. Parnell, J.C.S. (1962), 661] with a Grignard reagent represented by the formula:

$$R^4R^3R^2CMgZ^2 \quad XXII$$

(wherein $R^2$, $R^3$ and $R^4$ are as hereinbefore defined and $Z^2$ represents a halogen, preferably bromine, atom), or with a metal alkyl wherein the alkyl moiety corresponds to the group $CR^2R^3R^4$, for example an alkyl lithium, in an inert organic solvent, for example a lower dialkyl ether, e.g., diethyl ether.

Compounds of formula XVIII are prepared by the reduction of compounds of formula XVII, preferably by hydrogenation in the presence of a hydrogenation catalyst, e.g., Raney nickel, in the presence of an inert organic solvent, for example a lower alkanol, e.g., ethanol, preferably at elevated temperature and pressure, for example at 105°C. and a hydrogen pressure of 45 kilograms per square centimeter, or by treatment with a complex metal reducing agent, for example an alkali metal borohydride (e.g., sodium borohydride), in an aqueous organic solvent, for example an aqueous lower alkanol, e.g., ethanol, at temperatures between, for example, 0°C. and room temperature.

Compounds of formula XX are prepared by acylation of compounds of formula XVIII in conditions similar to those hereinbefore described for the acylation of the compounds of formula XII wherein $R^{11}$ represents a group of formula X and $R^{10}$ represents a hydrogen atom.

Compounds of formula XVIII are alternatively prepared by the reaction of compounds of formula XIX with a Grignard reagent or a metal alkyl as hereinbefore described for the preparation of compounds of formula XVII from compounds of formula XVI.

Compounds of formula XIX may be prepared by the reduction of compounds of formula XVI by means of a known complex metal reducing agent, preferably a dialkylaluminium hydride (e.g., di-isobutylaluminium hydride), in a dry inert organic solvent, for example an aromatic hydrocarbon (e.g., benzene) or an ether (e.g., diethyl ether), at temperatures between −80°C. and + 30° C.

Compounds of formula XXI are prepared by the aqueous acid hydrolysis of compounds of formula XX in conditions similar to those hereinbefore described for the hydrolysis of compounds of formula VI to form compounds of formula I.

Compounds of formula XIII are prepared by the reaction of compounds of formula XXI with an acylating agent, preferably a lower alkenyl acetate, for example isopropenyl acetate. The reaction is preferably carried out in the presence of an organic acid, for example p-toluenesulphonic acid, using an excess of the lower alkenyl acetate as a solvent, at an elevated temperature so as to maintain continuous removal of the alkanone formed during the reaction.

Compounds of formula V (wherein the various symbols are as hereinbefore defined in relation to that formula) with the exception of those compounds in which X and Y simultaneously represent a vinylene group and a carbonyl group respectively, are prepared by the reduction of compounds of formula V other than those compounds in which X and A simultaneously represent an ethylene group and a hydroxymethylene group respectively, with means and in conditions similar to those hereinbefore described for the reduction of compounds of formula Ib to form compounds of formula Ia.

Compounds of formula V wherein X represents a vinylene group, A and Y both represent carbonyl groups, and $R^1$ represents a hydrogen atom ($R^2$, $R^3$, $R^4$, $R^8$ and $n$ being as hereinbefore defined) (hereinafter referred to as "compounds of formula Va"), are prepared from compounds of formula VIII, wherein the symbols $R^{10}$ represent alkanoyl groups containing from 1 to 5 carbon atoms, and $R^{11}$ represents a group of formula X (hereinafter referred to as "compounds of formula VIIIa"), by the application of the following reaction sequence:

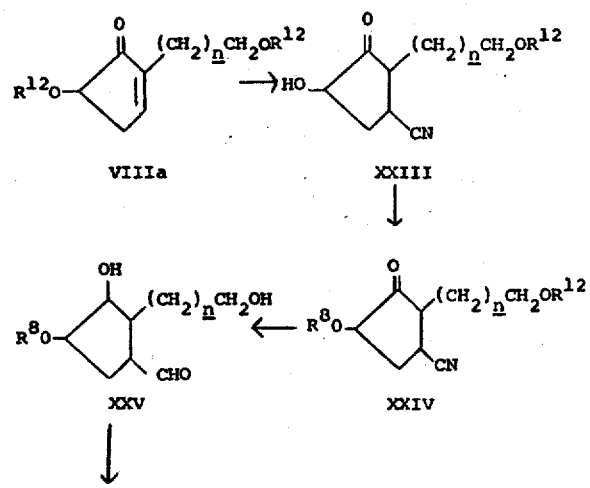

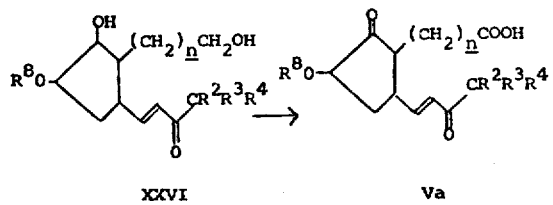

wherein $R^2$, $R^3$, $R^4$, $R^8$, $R^{12}$ and $n$ are as hereinbefore defined.

Thus, compounds of formula XXIII are prepared by the reaction of compounds of formula VIIIa with a source of hydrogen cyanide (e.g., acetone cyanohydrin) in the presence of a base, for example an alkali metal carbonate (e.g., sodium carbonate), preferably in an inert aqueous organic solvent, for example an aqueous lower alkanol (e.g. aqueous methanol). The reaction is preferably effected at 50° to 100°C. and advantageously at the reflux temperature of the reaction mixture.

Compounds of formula XXIV are prepared by the reaction of compounds of formula XXIII with 2,3-dihydropyran or the appropriate substituted (e.g., alkylated) 2,3-dihydropyran in the presence of a catalytic quantity of an acid, for example a mineral acid (e.g., concentrated hydrochloric acid). Reaction is preferably effected in the presence of an inert organic solvent, for example a halogenated hydrocarbon, e.g., dichloromethane, at a temperature between 15° and 75°C., preferably between 40° and 60°C.

Compounds of formula XXV are prepared by the simultaneous deacylation and reduction of compounds of formula XXIV. The reaction is preferably effected by treatment of compounds of formula XXIV with a complex metal reducing agent, preferably a dialkylaluminium hydride (e.g., di-isobutylaluminium hydride) in a dry inert organic solvent, for example a mixture of an ether (e.g., diethyl ether) and an aromatic hydrocarbon (e.g., benzene) and at temperatures between −80° and +30°C.

Compounds of formula XXVI are prepared by the reaction of compounds of formula XXV, either with compounds of the general formula:

$(R^{18})_3P=CHCOCR^2R^3R^4$   XXVII (wherein $R^2$, $R^3$ and $R^4$ are as hereinbefore defined, and $R^{18}$ represents an alkyl group or a phenyl group unsubstituted or substituted by an alkyl group, and advantageously represents a phenyl or n-butyl group), preferably in the presence of an inert organic solvent and preferably at a temperature between 20° and 100°C., for example in the presence of tetrahydrofuran as solvent at the reflux temperature of the reaction mixture or in the presence of hexamethylphosphotriamide as solvent at between 95° and 100°C., or preferably, with compounds of the general formula:

$(R^{19}O)_2P(O)CH_2COCR^2R^3R^4$   XXVIII (wherein $R^2$, $R^3$ and $R^4$ are as hereinbefore defined and $R^{19}$ represents an alkyl group of from 1 to 4 carbon atoms, preferably a methyl group), in the presence of a base, for example sodium hydride, and preferably in the presence of an inert organic solvent, for example an ether (e.g., tetrahydrofuran), and preferably at or near room temperature.

Compounds of formula Va are prepared by the oxidation of compounds of formula XXVI in conditions capable of oxidising hydroxymethyl groups to carboxy groups and hydroxymethylene groups to carbonyl groups without affecting carbon-carbon double bonds. The oxidation is, for example, effected by means of chromium trioxide and sulphuric acid in the presence of an inert organic solvent, for example dimethylformamide, at a temperature near or below the ambient temperature, for example at between −5°C. and +25°C., preferably in anhydrous conditions.

Compounds of formula V wherein $R^1$ represents an alkyl group $R^5$ as hereinbefore defined, are prepared by the esterification of compounds of formula V wherein $R^1$ represents a hydrogen atom by the action of an alcohol of formula II in conditions similar to those hereinbefore described for the esterification of compounds of formula I wherein $R^1$ represents a hydrogen atom by reaction with alcohols of formula II.

Compounds of formula XXVII may be prepared by the application or adaptation of known methods, for example by the reaction between compounds of the general formula:

$$Z^3CH_2COCR^2R^3R^4 \quad \quad XXIX$$

(wherein $R^2$, $R^3$ and $R^4$ are as hereinbefore defined and $Z^3$ represents a bromine or chlorine atom) and an appropriate trialkyl- or triphenyl-phosphine in a suitable organic solvent (e.g. chloroform) under a nitrogen atmosphere, preferably at a temperature of 20°–100°C. and advantageously at the reflux temperature of the reaction mixture, followed by reaction of the resulting 2-oxoalkylphosphonium halide with an inorganic base (e.g., aqueous sodium carbonate) at ambient temperature.

Compounds of formula XXVIII may be prepared by the application or adaptation of known methods, for example by the treatment of a compound of the general formula:

$$(R^{19}O)_2P(O)CH_3 \quad \quad XXX$$

(wherein $R^{19}$ is as hereinbefore defined) with butyl lithium at a low temperature, e.g., between −45° and −50°C., and in an inert organic solvent, e.g., a mixture of tetrahydrofuran and pentane followed by treatment of the resulting mixture, containing a compound of the general formula:

$$(R^{19}O)_2P(O)CH_2Li \quad \quad XXXI$$

(wherein $R^{19}$ is as hereinbefore defined), with a compound of the general formula:

$$R^{20}OOCCR^2R^3R^4 \quad \quad XXXII$$

(wherein $R^2$, $R^3$ and $R^4$ are as hereinbefore defined and $R^{20}$ represents an alkyl, preferably ethyl, group) at a temperature initially between −70° and −55°C. and subsequently rising to room temperature.

Compounds of formula VI wherein $R^1$ represents an alkyl group $R^5$ as hereinbefore defined (hereinafter referred to as "compounds of formula VIa") are prepared by the esterification of compounds of formula VI wherein $R^1$ represents a hydrogen atom (hereinafter referred to as "compounds of formula VIb") by the action of an alcohol of formula II in conditions similar to those hereinbefore described for the esterification of compounds of formula I wherein $R^1$ represents a hydrogen atom by reaction with alcohols of formula II.

Compounds of formula VIb are prepared from compounds of formula XXIII by the application of the following reaction sequence:

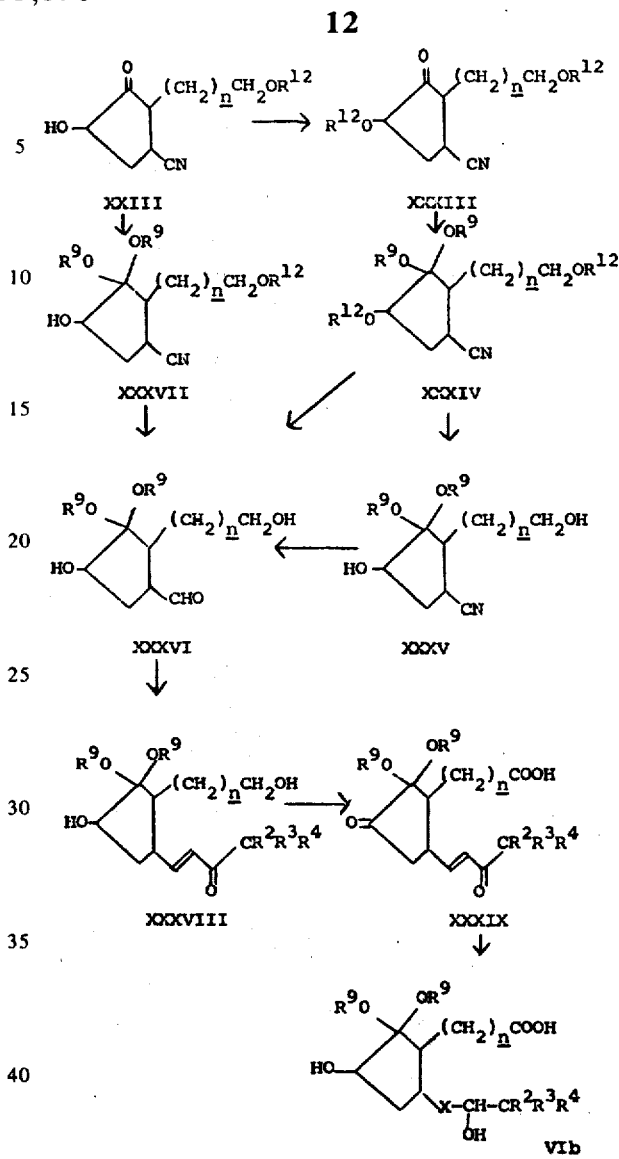

wherein the various symbols are as hereinbefore defined.

Thus, compounds of formula XXXIII are prepared by the acylation of compounds of formula XXIII, in similar conditions to those hereinbefore described for the acylation of compounds of formula XII wherein $R^{11}$ represents a group of formula X and $R^{10}$ represents a hydrogen atom.

Compounds of formula XXXIV are prepared from compounds of formula XXXIII by the application or adaptation of known methods for the preparation of ketals from ketones, for example by reaction with the appropriate alcohol or diol with an acidic catalyst, for example p-toluenesulphonic acid, preferably with continuous removal of water. Advantageously the reaction is effected in the presence of an inert organic solvent, for example an aromatic hydrocarbon (e.g. benzene), at an elevated temperature, such that the continuous removal of water is carried out by the use of an apparatus such as a Dean and Stark apparatus.

Compounds of formula XXXV are prepared by the alkaline hydrolysis of compounds of formula XXXIV, for example by the action of an alkali metal hydroxide (e.g., sodium hydroxide) in a mixture of water and an inert organic water-miscible solvent, for example a lower alkanol (e.g., ethanol), preferably at or near the ambient temperature.

Compounds of formula XXXVI are prepared by the reduction of compounds of formula XXXV or of compounds of formula XXXVII or XXXIV, with means and in conditions similar to those hereinbefore described for the preparation of compounds of formula XXV from compounds of formula XXIV.

Compounds of formula XXXVII are prepared from compounds of formula XXIII with similar means and conditions to those hereinbefore described for the preparation of compounds of formula XXXIV from compounds of formula XXXIII.

Compounds of formula XXXVIII are prepared by the reaction of compounds of formula XXXVI with compounds of formula XXVII or with compounds of formula XXVIII, in conditions similar to those hereinbefore described for the preparation of compounds of formula XXVI from compounds of formula XXV.

Compounds of formula XXXIX are prepared by the oxidation of compounds of formula XXXVIII with means and in conditions similar to those hereinbefore described for the oxidation of compounds of formula XXVI to form compounds of formula Va.

Compounds of formula VIb are prepared by the reduction of compounds of formula XXXIX in conditions similar to those hereinbefore described for the reduction of compounds of formula Ib to form compounds of formula Ia.

Thus, compounds of formula VIb wherein X represents a vinylene group are prepared by the reduction of compounds of formula XXXIX with means and in conditions similar to those hereinbefore described in (3) (a), and compounds of formula VIb wherein X represents an ethylene group are prepared by the reduction of compounds of formula XXXIX with means and in conditions similar to those hereinbefore described in (3)(c).

Compounds of formula VII wherein $R^1$ represents a hydrogen atom (hereinafter referred to as "compounds of formula VIIa") are prepared by the alkaline hydrolysis of compounds of formula VII wherein $R^1$ represents an alkyl group $R^5$ as hereinbefore defined (hereinafter referred to as "compounds of formula VIIb") with means and in conditions similar to those hereinbefore described in (2)(a).

Compounds of formula VIIb are prepared from compounds of formula VIII wherein the symbols $R^{10}$ represent alkanoyl groups $R^{12}$ as hereinbefore defined, and $R^{11}$ represents a group of formula IX (hereinafter referred to as "compounds of formula VIIIb") by the application of the following reaction sequence:

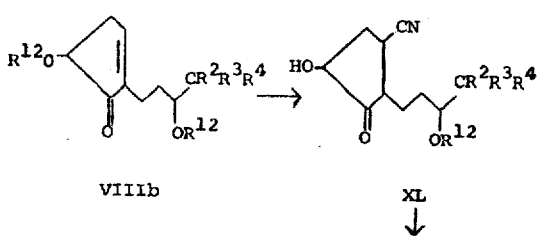

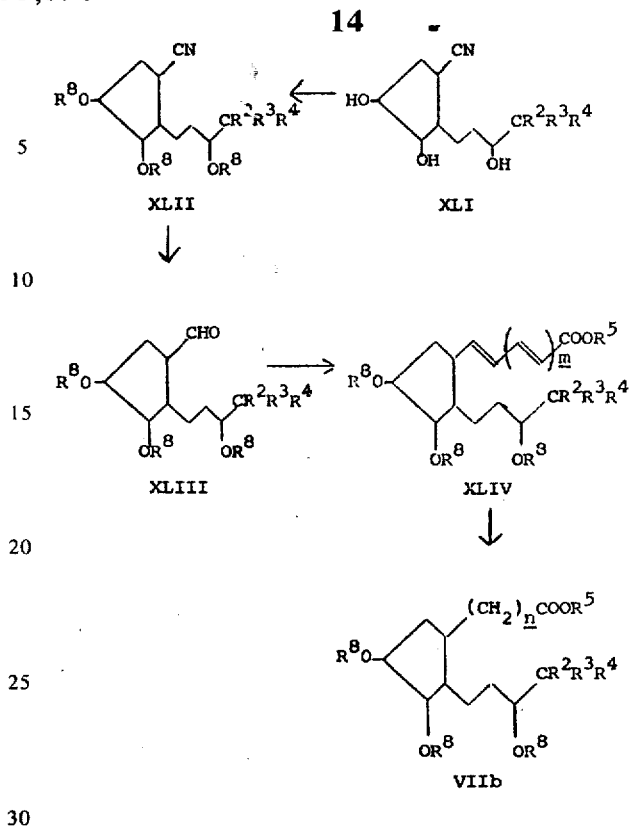

wherein $R^2$, $R^3$, $R^4$, $R^5$, $R^8$, $R^{12}$ and $n$ are as hereinbefore defined, and $m$ represents 1 or 2.

Thus, compounds of formula XL are prepared by the reaction of compounds of formula VIIIb with a source of hydrogen cyanide, in conditions similar to those hereinbefore described for the preparation of compounds of formula XXIII from compounds of formula VIIIa.

Compounds of formula XLI are prepared by the simultaneous deacylation and reduction of compounds of formula XL. The reaction is preferably effected by treatment of compounds of formula XL with an alkali metal borohydride, for example sodium borohydride or potassium borohydride, preferably in the presence of an aqueous alkali metal hydroxide, for example sodium hydroxide or potassium hydroxide, and, if desired, an inert organic solvent, for example a lower alkanol, e.g. methanol. The reaction is generally carried out at temperatures between −10°C. and +80°C., preferably initially at between −10° and +30°C. and then at an elevated temperature, preferably at between 50° and 60°C.

Compounds of formula XLII are prepared by the reaction of compounds of formula XLI with 2,3-dihydropyran or the appropriate substituted (e.g., alkylated) 2,3-dihydropyran, in conditions similar to those hereinbefore described for the preparation of compounds of formula XXIV from compounds of formula XXIII.

Compounds of formula XLIII are prepared by the reduction of compounds of formula XLII with means and in conditions similar to those hereinbefore described for the preparation of compounds of formula XXV from compounds of formula XXIV.

Compounds of formula XLIV are prepared by the reaction of compounds of formula XLIII with compounds of the general formula:

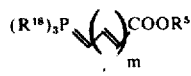 XLV wherein $R^5$, $R^{18}$ and $m$ are as hereinbefore defined. Reaction is preferably effected in the presence of an inert organic solvent, for example a halogenated hydrocarbon, e.g., chloroform, at temperatures between 0°C. and 30°C. under an inert atmosphere, e.g., nitrogen.

Compounds of formula VIIb are prepared by the reduction of compounds of formula XLIV, preferably by hydrogenation in the presence of a hydrogenation catalyst, for example palladium on charcoal, in the presence of an inert organic solvent, for example a lower alkanol, e.g., ethanol, and preferably at a temperature between 15° and 100°C. and at elevated pressure, for example at a hydrogen pressure of 15 kilograms per square centimeter and at between 15° and 40°C.

Compounds of formula XLV are prepared by the application or adaptation of known methods, for example by the treatment of compounds of the general formula:

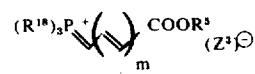 XLVI (wherein $R^5$, $R^{18}$, $m$ and $Z^3$ are as hereinbefore defined) with an inorganic base, for example an alkali metal hydroxide, e.g. sodium hydroxide, in water, at a temperature between 0°C. and 20°C., preferably between 0°C. and 4°C.

Compounds of formula XLVI are prepared by the reaction of compounds of the general formula:
$(R^{18})_3P$  XLVII
(wherein $R^{18}$ is as hereinbefore defined) with a compound of the general formula:

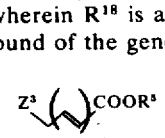 XLVIII (wherein $R^5$, $m$ and $Z^3$ are as hereinbefore defined) in a dry inert organic solvent, for example an aromatic hydrocarbon, e.g., benzene.

Compounds of formula XLVIII may be prepared by the methods described by Ziegler, Spath, Schaaf, Schumann and Winkelmann, Annalen, 551, (1942), 80, and Heilbron, Jones and O'Sullivan, J.C.S.; (1946), 866.

By the term "non-toxic salts," as used in this specification, is meant salts the cations of which are relatively innocuous to the animal organism when used in therapeutic doses so that the beneficial pharmacological properties of the parent acid compound of general formula I are not vitiated by side-effects ascribable to those cations. Preferably the salts are water-soluble. Suitable salts include the alkali metal, e.g., sodium and potassium, and ammonium salts and pharmaceutically-acceptable (i.e., non-toxic) amine salts.

Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from alkyl groups containing from 1 to 6 carbon atoms, hydroxyalkyl groups containing from 1 to 3 carbon atoms, cycloalkyl groups containing from 3 to 6 carbon atoms, phenyl groups, phenylalkyl groups containing from 7 to 11 carbon atoms and phenylalkyl groups containing from 7 to 15 carbon atoms wherein the alkyl moieties are substituted by hydroxy groups. The phenyl groups and phenyl moieties of such phenylalkyl groups may be unsubstituted or substituted by one or two alkyl groups containing from 1 to 6 carbon atoms. Suitable amines also include those derived in theory by the replacement of two of the hydrogen atoms of ammonia by a hydrocarbon chain, which may be interrupted by nitrogen, oxygen or sulphur atoms, to form, together with the nitrogen atom of ammonia to which its terminal groups are attached, a five- or six-membered nitrogen-containing heterocyclic ring, which heterocyclic ring may be unsubstituted or substituted by one or two alkyl groups containing from 1 to 6 carbon atoms. Examples of suitable amine cations include mono-, di- and tri-methylammonium, mono-, di- and tri-ethylammonium, mono-, di- and tri-propylammonium, mono-, di- and tri-isopropylammonium, ethyldimethylammonium, mono-, di- and tri-2-hydroxyethylammonium, ethyl-bis(2-hydroxyethyl)ammonium, butylmono(2-hydroxyethyl)-ammonium, tris(hydroxymethyl)methylammonium, cyclohexylammonium, benzylammonium, benzyldimethylammonium, dibenzylammonium, phenyl-2-hydroxyethylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-butylpiperidinium, 2-methylpiperidinium and 1-ethyl-2-methylpiperidinium.

The non-toxic salts may be prepared from parent compounds of formula I by known methods, for example by reaction of stoichiometric quantities of compounds of formula I (wherein $R^1$ represents a hydrogen atom) and the appropriate base, e.g., an alkali metal hydroxide or carbonate, ammonium hydroxide, ammonia or an amine, in a suitable solvent which is preferably water in the case of the preparation of alkali metal salts and water or isopropanol in the case of amine salts. The salts may be isolated by lyophilisation of the solution or, if sufficiently insoluble in the reaction medium, by filtration, if necessary after removal of part of the solvent.

As well as being useful in themselves as pharmaceutically useful compounds, salts of the compounds of formula I wherein $R^1$ represents a hydrogen atom are useful for the purposes of purification of the parent acids of formula I, for example by exploitation of the solubility differences between the salts and the parent acids in water and in organic solvents, by techniques well known to those skilled in the art. The parent acids of formula I can be regenerated from their salts by known methods, for example by treatment with a mineral acid, e.g. dilute hydrochloric acid.

It is to be understood that where in this specification reference is made to compounds of formula I, it is intended to refer also, where the context so permits, to the said salts of the compounds of formula I wherein $R^1$ represents a hydrogen atom.

As will be readily appreciated by those skilled in the art, the isomeric forms of the compounds of the invention arising from the aforementioned centres of chirality may be separated by the application or adaptation of known methods, for example diastereoisomeric forms may be separated by chromatography using selective adsorption from solution or from the vapour phase onto suitable adsorbents, and enantiomeric forms of acidic compounds of formula I wherein R¹ represents a hydrogen atom may be separated by formation of salts with an optically active base, followed by separation of the obtained pair of diastereoisomers by, for example, fractional crystallisation from a suitable solvent system, followed by separate regeneration of the enantiomeric acids of formula I.

By the term "known methods" as used in the present specification is meant methods heretofore used or described in the chemical literature.

Preferred classes of compounds of formula I according to the invention are:

i. compounds of formula 1 wherein A represents a methylene group, B represents a hydroxymethylene group, X represents an ethylene group and y represents a hydroxymethylene group;

ii. compounds of formula 1 wherein A represents a carbonyl or hydroxymethylene group, B represents a methylene group, X represents a trans-vinylene group, and Y represents a hydroxymethylene group or, when A represents a carbonyl group, a carbonyl group;

iii. compounds of formula I wherein R¹ represents a hydrogen atom or a methyl or ethyl group; and iv. compounds of formula I wherein R² represents a hydrogen atom, R³ represents a hydrogen atom or a methyl group, and R⁴ represents a propyl, butyl or hexyl group. Especially preferred compounds are:

7-[3,4-dihydroxy-2-(3-hydroxyoctyl)cyclopentyl]-heptanoic acid, and its methyl and ethyl esters and its sodium salt, 7-[2,3-dihydroxy-5-(3-hydroxyalk-1-enyl)cyclopentyl]-heptanoic acids, wherein the said alk-1-enyl moiety is an oct-1-enyl, hept-1-enyl, dec-1-enyl or 4-methyloct-1-enyl group, and 7-[3-hydroxy-2-oxo-5-(3-oxooct-1-enyl)cyclopentyl]-heptanoic acid.

The following Examples illustrate the preparation of new compounds of the present invention.

EXAMPLE 1 a. Preparation of 1,4-dioxa-6-(3-oxooctyl)spiro[4,4]nonane

A solution of 1,4-dioxa-6-(2-cyanoethyl)spiro[4,4-]nonane [prepared by the method described by T. Hensall and E. W. Parnell, J.C.S. (1962), 661](372 g.) in dry diethyl ether (1 liter) was added dropwise with stirring over 0.75 hours to pentyl magnesium bromide [1.5 equivalents, prepared by adding pentyl bromide (491 g.) in dry diethyl ether (750 ml.) to magnesium (90.6 g.) in dry diethyl ether (1.5 liters)]. The mixture was then refluxed for 2 hours and the cooled reaction mixture decomposed by careful addition of a saturated aqueous ammonium chloride solution, filtered, and the ether phase separated. The aqueous phase was extracted twice more with diethyl ether and the combined ether extracts dried over anhydrous magnesium sulphate. The diethyl ether was removed in vacuo and the residue distilled to give crude 1,4-dioxa-6-(3-oxooctyl)spiro[4,4]nonane, b.p. 110°–145°C./0.1 mm.Hg. This was redistilled to give 1,4-dioxa-6-(3-oxooctyl)-spiro[ 4,4]nonane (251 g.), b.p. 135°–140°C./0.05–0.1 mm.Hg; $n_D^{22} = 1.462$.

b. Preparation of 1,4-dioxa-6-(3-hydroxyoctyl)spiro[4,4]nonane 1,4-Dioxa-6-(3-oxooctyl)spiro[4,4]nonane (250 g.) [prepared as described in (a) above] in ethanol (100 ml.) was catalytically hydrogenated using Raney nickel (37.5 g., hydrogen pressure 45 kg./cm²) at 105°C. for 8 hours. After removal of the catalyst by filtration and evaporation of the ethanol in vacuo, the residue gave 1,4-dioxa-6-(3-hydroxyoctyl)spiro[4,4]nonane (230 g.), b.p. 120°–130°C./0.1–0.05 mm.Hg; $n_D^{24} = 1.4715$.

c. Preparation of 1,4-dioxa-6-(3-acetoxyoctyl)spiro[4,4]nonane 1,4-Dioxa-6-(3-hydroxyoctyl)spiro[4,4]nonane (229 g.) [prepared as described in (b) above] in acetic anhydride (1,150 ml.) was heated at 100°C for 2 hours. The excess acetic anhydride was removed in vacuo and the residue distilled to give 1,4-dioxa-6-(3-acetoxyoctyl)-spiro[4,4]nonane (245 g.), b.p. 140°–145°C./0.05 mm.Hg; $n_D^{26} = 1.458$.

d. Preparation of 2-(3-acetoxyoctyl)cyclopentanone 1,4-Dioxa-6-(3-acetoxyoctyl)spiro[4,4]nonane (244 g.) [prepared as described in (c) above], glacial acetic acid (960 ml.) and water (240 ml.) were allowed to stand at room temperature for 3 days with occasional shaking. The mixture was diluted with water (6 l.), extracted with diethyl ether and the ether extracts washed with water, saturated aqueous sodium bicarbonate, water and saturated aqueous sodium chloride solution. After drying over anhydrous magnesium sulphate and evaporation of the ether in vacuo, the residue was distilled to give 2-(3-acetoxyoctyl)cyclopentanone (179 g.), b.p. 120°–125°C./0.07 mm.Hg; $n_D^{26} = 1.456$.

e. Preparation of 1-acetoxy-2-(3-acetoxyoctyl)cyclopent-1-ene 2-(3-Acetoxyoctyl)cyclopentanone (85 g.) [prepared as described in (d) above], isopropenyl acetate (125 ml.) and p-toluenesulphonic acid (2 g.) were refluxed for 24 hours allowing the acetone formed during the reaction to slowly distil from the head of a Dufton column. The excess isopropenyl acetate was then distilled off and the residue cooled, shaken with 2N sodium carbonate solution and extracted with diethyl ether. The combined ether extracts were dried over anhydrous magnesium sulphate and the ether removed in vacuo. Distillation of the residue gave 1-acetoxy-2-(3-acetoxyoctyl)cyclopent-1-ene (85 g.), b.p. 108°–110°C./0.03 mm.Hg; $n_D^{26} = 1.459$.

f. Preparation of 2-(3-acetoxyoctyl)cyclopent-2-enone

To a stirred solution of 1-acetoxy-2-(3-acetoxyoctyl)cyclopent-1-ene (59.2 g.)[prepared as described in (e) above] in dry carbon tetrachloride (350 ml.) was added dropwise, during 30 minutes, a solution of bromine (32 g.) in dry carbon tetrachloride (100 ml.) at −10° to −5° C. The solution was stirred for a further 20 minutes without cooling. Triethylamine (22.2 g.) was then added and the resulting mixture stirred and refluxed for 90 minutes. The mixture was filtered, and the filtrate washed with aqueous 2N sodium carbonate and with water. After drying over magnesium sulphate and evaporation of the solvent in vacuo, the residue was distilled, in the presence of a few crystals of potassium acetate, at 132°–168°C./0.25 mm.Hg, to give crude 2-(3-acetoxyoctyl)cyclopent-2-enone. This was redistilled, with potassium acetate, at 116°–135°C./0.15 mm.Hg to give 2-(3-acetoxyoctyl)-cyclopent-2-enone (28.7 g.), $n_D^{28} = 1.470$.

g. Preparation of 2-(3-acetoxyoctyl)-2,3-epoxycyclopentanone

A stirred solution of 2-(3-acetoxyoctyl)cyclopent-2-enone (31.8 g.) [prepared as described in (f) above] in methanol (700 ml.) was treated slowly with aqueous hydrogen peroxide solution (45 ml. of "100 vol." solution) and aqueous 4N sodium hydroxide solution (15 ml.) at 5° to 10°C. and allowed to stand at room temperature for 18 hours. The solution was concentrated in vacuo (to about 100 ml. volume), and water (100 ml.) was added to the residue. The mixture was extracted with chloroform and the chloroform extract was washed with water and dried over magnesium sulphate. The solvent was removed in vacuo to give 2-(3-acetoxyoctyl)-2,3-epoxycyclopentanone (26.4 g.) which was used as starting material in the following preparation (h) of 5-acetoxy-2-(3-acetoxyoctyl)-cyclopent-2-enone without further purification.

h. Preparation of 5-acetoxy-2-(3-acetoxyoctyl)cyclopent-2-enone

A solution of 2-(3-acetoxyoctyl)-2,3-epoxycyclopentanone (26.8 g.)[prepared as described in (g) above] in glacial acetic acid (500 ml.) was heated at reflux for 12 hours. The excess acetic acid was then removed in vacuo and the residue distilled under reduced pressure to give 5-acetoxy-2-(3-acetoxyoctyl)cyclopent-2-enone (24.7 g.), b.p. 164°–175°C./0.2 mm.Hg.

j. Preparation of 2-(3-acetoxyoctyl)-3-cyano-5-hydroxycyclopentanone

5-Acetoxy-2-(3-acetoxyoctyl)cyclopent-2-enone (15.5 g.) [prepared as described in (h) above], acetone cyanohydrin (6.0 g.), aqueous sodium carbonate solution (10.0% w/v; 5 ml.) and methanol (75 ml.) were stirred together and heated at reflux for 4 hours. Methanol was removed in vacuo, water (50 ml.) was added and the mixture extracted with diethyl ether. The ethereal extract was washed with water, dried with magnesium sulphate and evaporated in vacuo to give 2-(3-acetoxyoctyl)-3-cyano-5-hydroxycyclopentanone (14.3 g.) which was used as starting material in the following preparation (k) of 3,4-dihydroxy-2-(3-hydroxyoctyl)cyclopentane carbonitrile without further purification.

k. Preparation of 3,4-dihydroxy-2-(3-hydroxyoctyl)-cyclopentane carbonitrile A stirred solution of 2-(3-acetoxyoctyl)-3-cyano-5-hydroxycyclopentanone (23.5 g.) [prepared as described in (j) above] in methanol (135 ml.) was treated dropwise, during 15 minutes, with a solution of sodium borohydride (13.2 g.) in 0.2N aqueous sodium hydroxide solution (70 ml.) at 15°–20°C. After 1 hour the solution was slowly heated to 50°C., stirred at 50°C. for 3 hours, and then allowed to stand at room temperature overnight. Methanol was removed in vacuo, water (75 ml.) was added and the mixture acidified by means of concentrated hydrochloric acid. The mixture was extracted with diethyl ether and the ethereal extract was washed with water, dried with magnesium sulphate and evaporated in vacuo to give crude 3,4-dihydroxy-2-(3-hydroxyoctyl)cyclopentane carbonitrile (16 g.), which was used in the following preparation (l) of 3,4-di(2-tetrahydropyranyloxy)-2-[3-(2-tetrahydropyranyloxy)octyl]cyclopentane carbonitrile without further purification.

An aliquot was distilled under reduced pressure to give 3,4-dihydroxy-2-(3-hydroxyoctyl)cyclopentane carbonitrile, b.p. 205°–220°C./0.1 mm.Hg. Elemental analysis: found: C, 65.9; H, 10.4%; $C_{14}H_{25}NO_3$ requires C, 65.8; H, 9.9%.

l. Preparation of 3,4-di(2-tetrahydropyranyloxy)-2-[3-(2-tetrahydropyranyloxy)octyl]cyclopentane carbonitrile 2,3-Dihydropyran (5.4 g.) was added dropwise at 40°C., with stirring, to a solution of 3,4-dihydroxy-2-(3-hydroxyoctyl)cyclopentane carbonitrile (4.0 g.) [prepared as described in (k) above] and concentrated hydrochloric acid (4 drops) in dichloromethane (5 ml.). The temperature was allowed to rise to 55°C., maintained at 55°C. for 2 hours and then cooled. Diethyl ether (50 ml.) was added, and the solution was washed with aqueous 2N sodium hydroxide and with water, dried over magnesium sulphate, and evaporated in vacuo to give crude 3,4-di(2-tetrahydropyranyloxy)-2-[3-(2-tetrahydropyranyloxy)octyl]cyclopentane carbonitrile (7.9 g.) which was used as starting material in the following preparation (m) of 3,4-di(2-tetrahydropyranyloxy)-2-[3-(2-tetrahydropyranyloxy)octyl]cyclopentane carbaldehyde without further purification.

m. Preparation of 3,4-di(2-tetrahydropyranyloxy)-2-[3(2-tetrahydropyranyloxy)octyl]cyclopentane carbaldehyde To a vigorously stirred solution of crude 3,4-di(2-tetrahydropyranyloxy)-2-[3-(2-tetrahydropyranyloxy)octyl]cyclopentane carbonitrile (7.9 g.) [prepared as described in (l) above] in dry diethyl ether (50 ml.) was added a solution of di-isobutylaluminium hydride (4.6 g.) in dry benzene (20 ml.) at 3°–7°C. The mixture was stirred at room temperature for 15 minutes and then added with stirring to aqueous 2N acetic acid solution (75 ml.) at below 15°C. The organic phase was separated, and the aqueous layer extracted with diethyl ether. The combined organic phases were washed with aqueous sodium bicarbonate and with water, dried over magnesium sulphate, and the solvents removed in vacuo to give crude 3,4-di(2-tetrahydropyranyloxy)-2-[3-(2-tetrahydropyranyloxy)octyl]cyclopentane carbaldehyde (7.7 g.), which was used as starting material in the following preparation (n) of ethyl 7-{3,4-di(2-tetrahydropyranyloxy)-2-[3-(2-tetrahydropyranyloxy)octyl]cyclopentyl} hepta-2,4,6-trienoate without further purification.

n. Preparation of ethyl 7-{3,4-di(2-tetrahydropyranyloxy)-2-[3-(2-tetrahydropyranyloxy)octyl]cyclopentyl} hepta-2,4,6-trienoate.

A solution of 5-ethoxycarbonylpenta-2,4-dienyltriphenylphosphorane [prepared by adding N aqueous sodium hydroxide solution (40 ml.) to a stirred solution of 5-ethoxycarbonylpenta-2,4-dienyltriphenylphosphonium bromide (16.4 g.) in water (1000ml.) at 1°–3°C., extracting with chloroform and concentrating the extract to about 250 ml.] was treated at 2°C. under nitrogen with a solution of 3,4-di(2-tetrahydropyranyloxy)-2-[3-(2-tetrahydropyranyloxy)octyl]-cyclopentane carbaldehyde (8.5 g.) [prepared as described in (m) above] in chloroform (20 ml.). The solution was allowed to stand at room temperature for 18 hours, the chloroform was removed in vacuo, and the residue extracted three times with hot petroleum ether (b.p. 40°–60°C.). The combined petroleum extracts were cooled and filtered to remove precipitated triphenylphosphine oxide. The filtrate was evaporated in vacuo and the residue separated by chromatography on silica gel. Elution with petroleum ether (b.p. 40°–60°C.) gave ethyl 7-{3,4-di(2-tetrahydropyranyloxy)-2-[3-(2 -tetrahydropyranyloxy)octyl]-cyclopentyl}-hepta-2,4,6-trienoate (6.4 g.), $\nu_{max}$: 1700 cm$^{-1}$, 1610 cm$^{-1}$ (liquid film).

5-Ethoxycarbonylpenta-2,4-dienyltriphenylphosphonium bromide, used as a starting material, was prepared as follows:

To a stirred solution of triphenylphosphine (34 g.) in dry benzene (300 ml.) was added ethyl 6-bromohexa-2,4-dienoate (30 g.). After 18 hours, the benzene was decanted from the precipitated paste which solidified on adding diethyl ether and was ground up and filtered to give 5-ethoxycarbonylpenta-2,4-dienyltriphenylphosphonium bromide (40 g.), m.p. 139°–144°C.

o. Preparation of ethyl 7-{3,4-di(2-tetrahydropyranyloxy)-2-[3-(2-tetrahydropyranyloxy)octyl]cyclopentyl}heptanoate.

Ethyl 7-{3,4-di(2-tetrahydropyranyloxy)-2-[3-(2-tetrahydropyranyloxy)octyl]cyclopentyl}hepta-2,4,6-trienoate (6.1 g.) [prepared as described in (n) above] was dissolved in ethanol (100 ml.) and catalytically hydrogenated using a 5% palladium on charcoal catalyst, with a hydrogen pressure of 15 kg./cm$^2$, at room temperature. The catalyst was then filtered off and the ethanol removed in vacuo to give ethyl 7-{3,4-di(2-tetrahydropyranyloxy)-2-[3-(2-tetrahydropyranyloxy)octyl]cyclopentyl}heptanoate (5.7 g.), which was used as starting material in the following preparation (p) of ethyl 7-[3,4-dihydroxy-2-(3-hydroxyoctyl)cyclopentyl]heptanoate without further purification.

p. Preparation of ethyl 7-[3,4-dihydroxy-2-(3-hydroxyoctyl)cyclopentyl]heptanoate.

A mixture of ethyl 7-{3,4-di(2-tetrahydropyranyloxy)2-[3-(2-tetrahydropyranyloxy)octyl]cyclopentyl-}heptanoate (5.5 g.) [prepared as described in (o) above], ethanol (100 ml.), N hydrochloric acid (100 ml.) and a cation- exchange resin [Dowex resin AG50w - X8H$^+$ (7.5 g.) ] was stirred at 50°–50°C. for 18 hours. The mixture was then cooled and filtered and the solid washed with diethyl ether and water. The combined filtrate and washings were evaporated in vacuo to remove organic solvents and the aqueous residue extracted with diethyl ether. The ethereal extract was dried over anhydrous sodium carbonate and evaporated in vacuo to give ethyl 7-[3,4-dihydroxy-2-(3-hydroxyoctyl)cyclopentyl]heptanoate (3.2 g.), which was used as starting material in the following preparation (q) of 7-[3,4-dihydroxy-2-(3-hydroxyoctyl)cyclopentyl]heptanoic acid without further purification.

Ethyl 7-[3,4-dihydroxy-2-(3-hydroxyoctyl)cyclopentyl]heptanoate is a compound of formula I.

q. Preparation of 7-[3,4-dihydroxy-2-(3-hydroxyoctyl)cyclopentyl]heptanoic acid

Ethyl 7-[3,4-dihydroxy-2-(3-hydroxyoctyl)cyclopentyl]heptanoate (2.6 g.) [prepared as described in (p) above], ethanol (50 ml.) and 2N aqueous sodium hydroxide solution (50 ml.) were heated together at reflux for 18 hours. The ethanol was removed in vacuo, water (25 ml.) was added and the mixture was washed with diethyl ether. The aqueous phase {which has a solution of sodium 7-[3,4-dihydroxy-2-(3-hydroxyoctyl)cyclopentyl]heptanoate} was acidified to pH 1 by the dropwise addition of concentrated hydrochloric acid, extracted with diethyl ether, and the ethereal extract dried over magnesium sulphate and evaporated in vacuo to give 7-[3,4-dihydroxy-2-(3-hydroxyoctyl)-cyclopentyl]heptanoic acid (1.1 g.).

Elemental analysis: found: C, 67.2; H, 10.3%. $C_{20}H_{38}O_5$ requires C, 67.0; H, 10.7%.

The nuclear magnetic resonance spectrum (N.M.R.) of a 10% solution of the 7-[3,4-dihydroxy-2-(3-hydroxyoctyl)cyclopentyl]heptanoic acid in deuterochloroform at 60°C. displayed the following peaks:

triplet at 0.89δ, J = 4.5 cycles/second (terminal methyl group);

broad peak, maximum at 1.39δ (chain methylene groups);

multiplets at 1.4–2.1δ (ring methylene and methylidene groups);

triplet at 2.31δ, J = 6.5 cycles/second (methylene next to carboxy);

peaks at 3.62δ and 3.95δ (3 hydrogen atoms in methylidene groups attached to hydroxy groups);

peak at 5.06δ (4 hydrogen atoms in hydroxy and carboxy groups).

EXAMPLE 2 a. Preparation of 2,3-epoxy-2-(7-hydroxyheptyl)cyclopentanone

By proceeding in a similar manner to that described above in Example 1(g) for the preparation of 2-(3-acetoxyoctyl)-2,3-epoxycyclopentanone, but substituting the appropriate quantity of 2-(7-hydroxyheptyl)cyclopent-2-enone for the 2-(3-acetoxyoctyl)cyclopent-2-enone used as starting material, there was prepared, 2,3-epoxy-2-(7-hydroxyheptyl)cyclopentanone, $\nu_{max}$. 3425 cm$^{-1}$, 1730 cm$^{-1}$.

The 2-(7-hydroxypentyl)cyclopent-2-enone, used as starting material, was prepared as follows:

A mixture of 7-(2-tetrahydropyranyloxy)heptanal (22 g.) and 1-morpholinocyclopentene, i.e. the morpholine enamine of cyclopentanone, (21.4 g.) in benzene (25 ml.) was heated under reflux for 12 hours under nitrogen, and the water liberated was continuously removed with a Dean and Stark head. Benzene (10 ml.) and then, dropwise, 18% hydrochloric acid (28 ml.) were added and the mixture was stirred for 2 hours. The organic layer was separated and evaporated. Concentrated hydrochloric acid (72 ml.) was added to the residue. The mixture was heated at 100°C. for 1 hour, and then the solution was concentrated to give an oil. Diethyl ether was added, and the ether solution was washed with aqueous sodium bicarbonate and then water, and dried over sodium sulphate. The solvent was evaporated and the residue was distilled under reduced pressure to give 2-(7-hydroxyheptyl)cyclopent-2-enone (11.7 g.), b.p. 125°–170°C./0.15 mm.Hg, $n_D^{25}$ = 1.490, $\lambda_{max}$ 228mμ (ethanol).

b. Preparation of 5-acetoxy-2-(7-acetoxyheptyl)cyclopent-2-enone

By proceeding in a similar manner to that described above in Example 1(h) for the preparation of 5-acetoxy-2-(3-acetoxyoctyl)cyclopent-2-enone, but substituting the appropriate quantity of 2,3-epoxy-2-(7-hydroxyheptyl)cyclopentanone [prepared as described above in Example 2(a)] for the 2-(3-acetoxyoctyl)-2,3-epoxycyclopentanone used as starting material, there was prepared 5-acetoxy-2-(7-acetoxyheptyl)cyclopent-2-enone, b.p. 172°–175°C./0.15 mm.Hg, $\nu_{max}$ 1730 cm$^{-1}$, 1710 cm$^{-1}$, 1235 cm$^{-1}$.

The nuclear magnetic resonance spectrum (N.M.R.) of a 10% solution of the 5-acetoxy-2-(7-acetoxyheptyl)cyclopent-2-enone in deuterochloroform displayed the following peaks:

broad peak at 1.05–1.95δ (5 methylene groups in middle of chain)
singlets at 2.05δ and 2.15δ (acetoxy groups)
multiplets at 1.95–2.7δ and at 3.1δ (ring methylene group and the chain methylene group adjacent to the ring)
triplet at 4.05δ (chain methylene group adjacent to acetoxy group)
doublet of doublets at 5.15δ (ring methylidene group adjacent to acetoxy group)
multiplet at 7.15–7.35δ (vinylene group).

c. Preparation of 2-(7-acetoxyheptyl)-3-cyano-5-hydroxycyclopentanone

By proceeding in a similar manner to that described above in Example 1(j) for the preparation of 2-(3-acetoxyoctyl)-3-cyano-5-hydroxycyclopentanone, but substituting the appropriate quantity of 5-acetoxy-2-(7-acetoxyheptyl)cyclopent-2-enone [prepared as described above in Example 2(b)] for the 5-acetoxy-2-(3-acetoxyoctyl)cyclopent-2-enone used as a starting material, there was prepared 2-(7-acetoxyheptyl)-3-cyano-5-hydroxycyclopentanone, $\nu_{max}$ 3425 cm$^{-1}$, 2250 cm$^{-1}$, 1730 cm$^{-1}$, 1240 cm$^{-1}$.

d. Preparation of 2-(7-acetoxyheptyl)-3-cyano-5-(2-tetrahydropyranyloxy)cyclopentanone.

By proceeding in a similar manner to that described above in Example 1(l) for the preparation of 3,4-di(2-tetrahydropyranyloxy)-2-[3-(2-tetrahydropyranyloxy)octyl]cyclopentane carbonitrile, but substituting the appropriate quantity of 2-(7-acetoxyheptyl)-3-cyano-5-hydroxycyclopentanone [prepared as described above in Example 2(c)] for the 3,4-dihydroxy-2-(3-hydroxyoctyl)cyclopentane carbonitrile used as a starting material, there was prepared 2-(7-acetoxyheptyl)-3-cyano-5-(2-tetrahydropyranyloxy)cyclopentanone, $\nu_{max}$ 2240 cm$^{-1}$, 1735 cm$^{-1}$, 1245 cm$^{-1}$.

e. Preparation of 3-formyl-2-(7-hydroxyheptyl)-5(2-tetrahydropyranyloxy)cyclopentanol By proceeding in a similar manner to that described above in Example 1(m) for the preparation of 3,4-di(2-tetrahydropyranyloxy)-2-[3-(2-tetrahydropyranyloxy)octyl]cyclopentane carbaldehyde, but substituting the appropriate quantity of 2-(7-acetoxyheptyl)-3-cyano-5-(2-tetrahydropyranyloxy)cyclopentanone [prepared as described above in Example 2(d)] for the 3,4-di(2-tetrahydropyranyloxy)-2-[3-(2-tetrahydropyranyloxy)octyl]cyclopentane carbonitrile used as starting material, there was prepared 3-formyl-2-(7-hydroxyheptyl(-5-(2-tetrahydropyranyloxy)cyclopentanol, $\nu_{max}$ 3400 cm$^{-1}$, 1710 cm$^{-1}$.

f. Preparation of 2-(7-hydroxyheptyl)-3-(3-oxoalk-1-enyl)-5-(2-tetrahydropyranyloxy)cyclopentanols A mixture of 3-formyl-2-(7-hydroxyheptyl)-5-(2-tetrahydropyranyloxy)cyclopentanol [5.4 g.; prepared as described above in Example 2(e)] and hexanoylmethylene triphenylphosphorane (5.6 g.) in dry tetrahydrofuran (60 ml.) was heated under reflux under nitrogen for 24 hours. The solvent was then removed in vacuo and the resulting residue was chromatographed on silica gel. Elution with diethyl ether gave 2-(7-hydroxyheptyl)-3-(3-oxooct-1-enyl)-5-(2-tetrahydropyranyloxy)-cyclopentanol (3.64g.), $\nu_{max}$ 3450 cm$^{-1}$, 1670 cm$^{-1}$, 1630 cm$^{-1}$, 985 cm$^{-1}$.

By proceeding in a similar manner, but substituting the appropriate quantity of pentanoylmethylene triphenylphosphorane for the hexanoylmethylene triphenylphosphorane used as a starting material, there was prepared 2-(7-hydroxyheptyl)-3-(3-oxohept-1-enyl)-5-(2-tetrahydropyranyloxy)cyclopentanol.

By again proceeding in a similar manner, but substituting the appropriate quantity of octanoylmethylene triphenylphosphorane for the hexanoylmethylene triphenylphosphorane used as a starting material, there was prepared 2-(7-hydroxyheptyl)-3-(3-oxodec-1-enyl)-5-(2-tetrahydropyranyloxy)cyclopentanol.

The hexanoylmethylene triphenylphosphorane, used as starting material, was prepared as follows:

A solution of 1-chloroheptan-2-one (33 g.) and triphenylphosphine (60 g.) in chloroform (50 ml.) was saturated with nitrogen and refluxed under nitrogen overnight. The chloroform was removed in vacuo and the residue was dissolved in methylene chloride (150 ml.). Dry diethyl ether (600 ml.) was added to precipitate 2-oxoheptyltriphenylphosphonium chloride (60 g.), m.p. 165°–168°C. This compound (23 g.) was added portionwise to a solution of sodium carbonate (25 g.) in water (250 ml.) and the mixture was stirred vigorously for 24 hours. The solution was extracted with diethyl ether, and the ethereal extracts were dried over magnesium sulphate. The solvent was removed by evaporation and the residue was cooled and triturated with petroleum ether (b.p. 40°–60°C.). The solid thus obtained was recrystallised from petroleum ether (b.p. 60°–80°C.) to give hexanoylmethylene triphenylphosphorane (17 g.), m.p. 73°–74°C.

The pentanoylmethylene triphenylphosphorane, m.p. 54°–56°C., used as a starting material, was prepared by proceeding in a similar manner but substituting the appropriate quantity of 1-chlorohexan-2-one for the 1-chloroheptan-2-one. The melting point of the intermediate 2-oxohexyltriphenylphosphonium chloride was 179°–181°C.

The octanoylmethylene triphenylphosphorane, m.p. 74°–76°C., used as a starting material, was prepared by again proceeding in a similar manner, but substituting the appropriate quantity of 1-chlorononan-2-one for the 1-chloroheptan-2-one. The melting point of the intermediate 2-oxononyltriphenylphosphonium chloride was 205°–207°C.

g. Preparation of 7-[2-oxo-5-(3-oxoalk-1-enyl)-3-(2-tetrahydropyranyloxy)cyclopentyl]heptanoic acids Chromium trioxide (4.0 g.) (dried over phosphorus pentoxide) was added portionwise to a stirred solution of 2-(7-hydroxyheptyl)-3-(3-oxooct-1-enyl)-5-(2-tetrahydropyranyloxy)cyclopentanol [2.12 g.; prepared as described in Example 2(f)] in dry dimethylformamide (30 ml.), while maintaining the temperature at between 5° and 15°C. A solution of concentrated sulphuric acid (1.4 ml.) in dimethylformamide (40 ml.) was then added and the mixture was stirred at between 5° and 15°C. for a further 90 minutes. Diethyl ether was then added, followed by a minimum quantity of water to produce two readily separable layers. The ethereal layer was separated and stirred with an aqueous 2N sodium carbonate solution. This aqueous layer was then separated, washed with diethyl ether, and then treated with a further quantity of diethyl ether and acidified to pH 4 by the dropwise addition of concentrated hydrochloric acid. The resulting ethereal layer was separated, and the remaining aqueous layer was extracted with a further quantity of diethyl ether. These last two ethereal solutions were then combined, dried over magnesium sulphate, and evaporated to dryness, to give crude 7-[2-oxo-5-(3-oxooct-1-enyl)-3-(2-tetrahydropyranyloxy)cyclopentyl]heptanoic acid (1.03 g.), $\nu_{max}$ 1720 cm$^{-1}$, 1700 cm$^{-1}$, 1670 cm$^{-1}$, 1625 cm$^{-1}$, 985 cm$^{-1}$, which was used as starting material in the following preparation (h) of 7-[2-hydroxy-5-(3-hydroxyoct-1-enyl)-3-(2-tetrahydropyranyloxy)cyclopentyl]heptanoic acid, without further purification being necessary.

By proceeding in a similar manner, but substituting the appropriate quantity of 2-(7-hydroxyheptyl)-3-(3-oxohept-1-enyl)-5-(2-tetrahydropyranyloxy)cyclopentanol [prepared as described above in Example 2(f)] for the 2-(7-hydroxyheptyl)-3-(3-oxooct-1-enyl)-5-(2-tetrahydropyranyloxy)cyclopentanol used as starting material, there was prepared 7-[2-oxo-5-(3-oxohept-1-enyl)-3-(2-tetrahydropyranyloxy)cyclopentyl]heptanoic acid, $\nu_{max}$ 1720 cm$^{-1}$, 1700 cm$^{-1}$, 1670 cm$^{-1}$, 1625 cm$^{-1}$, 985 cm$^{-1}$.

By again proceeding in a similar manner, but substituting the appropriate quantity of 2-(7-hydroxyheptyl)-3-(3-oxodec-1-enyl)-5-(2-tetrahydropyranyloxy)cyclopentanol [prepared as described above in Example 2(f)] for the 2-(7-hydroxyheptyl)-3-(3-oxooct-1-enyl)-5-(2-tetrahydropyranyloxy)cyclopentanol used as starting material, there was prepared 7-[2-oxo-5-(3-oxodec-1-enyl)-3-(2-tetrahydropyranyloxy)cyclopentyl]heptanoic acid, $\nu_{max}$ 1725 cm$^{-1}$, 1700 cm$^{-1}$, 1670 cm$^{-1}$, 1625 cm$^{-1}$, 985 cm$^{-1}$.

h. Preparation of 7-[2-hydroxy-5-(3-hydroxyalk-1-enyl)-3-(2-tetrahydropyranyloxy)cyclopentyl]heptanoic acids A solution of 7-[2-oxo-5-(3-oxooct-1-enyl)-3-(2-tetrahydropyranyloxy)cyclopentyl]heptanoic acid [0.45 g.; prepared as described above in Example 2(g)] in methanol (10 ml.) was added to a stirred 2% w/v aqueous solution of sodium citrate (100 ml.) at −5°C. Potassium borohydride (1.6 g.) was then added portionwise, allowing the pH to change to pH 8 and then maintaining at pH 8 by the addition, when necessary, of quantities of 10% w/v aqueous citric acid solution. When the addition of the potassium borohydride was complete, the solution was stirred for 90 minutes, meanwhile maintaining the pH at pH 8 by means of the addition of further quantities of the citric acid solution, and allowing it to attain room temperature. The solution was then treated with acetone (50 ml.), treated with a further quantity of the citric acid solution to bring the pH to pH 4, saturated with sodium chloride and extracted three times with diethyl ether. The combined ethereal extracts were washed with a saturated solution of sodium chloride in 2N hydrochloric acid, and then with a saturated aqueous solution of sodium chloride, and dried over magnesium sulphate. The solvent was removed in vacuo to give crude 7-[2-hydroxy-5-(3-hydroxyoct-1-enyl)-3-(2-tetrahydropyranyloxy)cyclopentyl]heptanoic acid (0.34 g.), $\nu_{max}$ 1700 cm$^{-1}$, 980 cm$^{-1}$, which was used as starting material in the following preparation (i) of 7-[2,3-dihydroxy-5-(3-hydroxyoct-1-enyl)cyclopentyl]heptanoic acid without further purification being necessary.

By proceeding in a similar manner, but substituting 7-[2-oxo-5-(3-oxohept-1-enyl)-3-(2-tetrahydropyranyloxy)cyclopentyl]heptanoic acid [prepared as described above in Example 2(g)] for the 7-[2-oxo-5-(3-oxooct-1-enyl)-3-(2-tetrahydropyranyloxy)cyclopentyl]heptanoic acid used as starting material, there was prepared 7-[2-hydroxy-5-(3-hydroxyhept-1-enyl)-3-(2-tetrahydropyranyloxy)cyclopentyl]heptanoic acid, $\nu_{max}$ 1705 cm$^{-1}$, 980 cm$^{-1}$.

By again proceeding in a similar manner, but substituting 7-[2-oxo-5-(3-oxodec-1-enyl)-3-(2-tetrahydropyranyloxy)cyclopentyl]heptanoic acid [prepared as described above in Example 2(g)] for the 7-[2-oxo-5-(3-oxooct-1-enyl)-3-(2-tetrahydropyranyloxy)cyclopentyl]heptanoic acid used as starting material, there was prepared 7-[2-hydroxy-5-(3-hydroxydec-1-enyl)-3-(2-tetrahydropyranyloxy)cyclopentyl]heptanoic acid, $\nu_{max}$ 1705 cm$^{-1}$, 980 cm$^{-1}$.

i. Preparation of 7-[2,3-dihydroxy-5-(3-hydroxyalk-1-enyl)cyclopentyl]heptanoic acids A mixture of 7-[2-hydroxy-5-(3-hydroxyoct-1-enyl)-3-(2-tetrahydropyranyloxy)cyclopentyl]heptanoic acid [0.34 g.; prepared as described above in Example 2(h)], ethanol (10 ml.), N aqueous hydrochloric acid (10 ml.) and a cation exchange resin [Dowex resin AG50W-X 8H$^+$ (1.0 g.)] was stirred at 60°–62°C. for 8 hours. The mixture was filtered and the solid was washed with ethanol. The combined filtrate and washings were concentrated in vacuo to remove most of the ethanol, and the residue was extracted twice with diethyl ether. The combined ethereal extracts were extracted with 2N aqueous sodium carbonate solution, and the aqueous extract was acidified to pH 1 by the addition of concentrated hydrochloric acid. The resulting aqueous mixture was extracted with diethyl ether and the ethereal extract was dried over magnesium sulphate and evaporated to dryness. The residue (0.13 g.) was subjected to preparative thin-layer chromatography on silica gel, using a mixture of ethyl acetate, cyclohexane and formic acid (40:40:1 by volume) as the eluent, to give 7-[2,3-dihydroxy-5-(3-hydroxyoct-1-enyl)cyclopentyl]-heptanoic acid (0.01 g.), $\nu_{max}$ 1700 cm$^{-1}$, 980 cm$^{-1}$. Elemental analysis: found: C, 67.8; H, 10.4%; $C_{20}H_{36}O_5$ requires C, 67.4; H, 10.2%.

By proceeding in a similar manner but substituting 7-[2-hydroxy-5-(3-hydroxyhept-1-enyl)-3-(2-tetrahydropyranyloxy)cyclopentyl]heptanoic acid [prepared as described above in Example 2(h)] for the 7-[2-hydroxy-5-(3-hydroxyoct-1-enyl)-3-(2-tetrahydropyranyloxy)cyclopentyl]heptanoic acid used as starting material, there was prepared 7-[2,3-dihydroxy-5-(3-hydroxyhept-1-enyl)cyclopentyl]heptanoic acid, $\nu_{max}$ 3400 cm$^{-1}$, 1700 cm$^{-1}$, 980 cm$^{-1}$.

By again proceeding in a similar manner, but substituting 7-[2-hydroxy-5-(3-hydroxydec-1-enyl)-3-(2-tetrahydropyranyloxy)cyclopentyl]heptanoic acid [prepared as described above in Example 2(h)] for the 7-[2-hydroxy-5-(3-hydroxyoct-1-enyl)-3-(2-tetrahydropyranyloxy)cyclopentyl]heptanoic acid used as starting material, there was prepared 7-[2,3-dihydroxy-5-(3-hydroxydec-1-enyl)cyclopentyl]heptanoic acid, $\nu_{max}$ 3400 cm$^{-1}$, 1700 cm$^{-1}$, 975 cm$^{-1}$.

EXAMPLE 3

Preparation of methyl 7-[3,4-dihydroxy-2-(3-hydroxyoctyl)cyclopentyl]heptanoate

A solution of diazomethane (60 mg.) in diethyl ether (10 ml.) was added to 7-[3,4-dihydroxy-2-(3-hydroxyoctyl)cyclopentyl]heptanoic acid (0.3 g.; prepared as described in Example 1(q)) and the reaction mixture was left to stand for one day at room temperature. The polymethylenes formed as by-products of the reaction were removed by filtration and the filtrate was washed with dilute aqueous sodium carbonate solution. Evaporation of the ethereal solution gave crude methyl 7-[3,4-dihydroxy-2-(3-hydroxyoctyl)cyclopentyl]heptanoate (0.26 g.), $\nu_{max}$ 3450 cm$^{-1}$, 1730 cm$^{-1}$.

EXAMPLE 4 a. Preparation of 2-(7-hydroxyheptyl)-3-(4-methyl-3-oxooct-1-enyl)-5-(2-tetrahydropyranyloxy)cyclopentanol A solution of dimethyl 3-methyl-2-oxoheptylphosphonate (2.36 g.) in tetrahydrofuran (20 ml.) was added dropwise to a stirred suspension of sodium hydride (0.24 g.) in tetrahydrofuran (50 ml.). The mixture was stirred at room temperature until the evolution of hydrogen had ceased, then treated dropwise with a solution of 3-formyl-2-(7-hydroxyheptyl)-5-(2-tetrahydropyranyloxy)cyclpentanol [3.28 g.; prepared as described above in Example 2(e)] in tetrahydrofuran (20 ml.) and stirred for a further 2 hours. The mixture was acidified to pH 4 by the addition of glacial acetic acid, the solvent was removed in vacuo and the residue dissolved in diethyl ether. The ethereal solution was washed with aqueous sodium carbonate solution, dried over magnesium sulphate, and evaporated to dryness to give 2-(7-hydroxyheptyl)-3-(4-methyl-3-oxooct-1-enyl)-5-(2-tetrahydropyranyloxy)cyclopentanol (4.1 g.).

The dimethyl 3-methyl-2-oxoheptylphosphonate used as a starting material was prepared as follows:

A stirred solution of dimethyl methylphosphonate (54 g.) in dry tetrahydrofuran (390 ml.) at $-45°$ to $-50°C$. was treated, dropwise during 20 minutes, with a solution of butyl lithium (32 g.) in pentane (250 ml.). Stirring was continued at that temperature for a further 10 minutes, and then the mixture was cooled to $-60°C$. and treated, dropwise during 15 minutes, with a solution of ethyl 2-methylhexanoate (34.5 g.) in tetrahydrofuran (120 ml.). The mixture was stirred at $-60°C$. for a further 90 minutes and then at room temperature for 3 hours, and then it was treated with acetic acid (42 ml.), evaporated to dryness in vacuo, and residue treated with water (170 ml.). The mixture was extracted twice with diethyl ether and the combined ethereal extracts washed with water, dried over sodium sulphate and evaporated to dryness in vacuo. The residue was distilled to give dimethyl 3-methyl-2-oxoheptylphosphonate (16.8 g.), b.p. 93–94°C./0.2mm.Hg.

Elemental analysis: found: C,50.8; H,9.0; P,12.7%; $C_{10}H_{21}PO_4$ requires C,50.9; H,8.9; P,13.1% b. Preparation of 7-[2-oxo-5-(4-methyl-3-oxooct-1-enyl)-3-(2-tetrahydropyranyloxy)cyclopentyl]heptanoic acid By proceeding in a similar manner to that described above in Example 2(g) for the preparation of 7-[2-oxo-5-(3-oxooct-1-enyl)-3-(2-tetrahydropyranyloxy)cyclopentyl]heptanoic acid, but substituting the appropriate quantity of 2-(7-hydroxyheptyl)-3-(4-methyl-3-oxooct-1-enyl)-5-(2-tetrahydropyranyloxy)cyclopentanol [prepared as described above in Example 4(a)] for the 2-(7-hydroxyheptyl)-3-(3-oxooct-1-enyl)-5-(2-tetrahydropyranyloxy)cyclopentanol used as starting material, there was prepared 7-[2-oxo-5-(4-methyl-3-oxooct-1-enyl)-3-(2-tetrahydropyranyloxy)cyclopentyl]heptanoic acid $\nu_{max}$ 1700cm$^{-1}$, 1670cm$^{-1}$, 1620cm$^{-1}$, 980cm$^{-1}$.

c. Preparation 7-[2-hydroxy-5-(3-hydroxy-4-methyloct-1-enyl)-3-(2-tetrahydropyranyloxy)cyclopentyl]heptanoic acid By proceeding in a similar manner to that described above in Example 2(h) for the preparation of 7-[2-hydroxy-5-(3-hydroxyoct-1-enyl)-3-(2-tetrahydropyranyloxy)cyclopentyl]heptanoic acid, but substituting the appropriate quantity of 7-[2-oxo-5-(4-methyl-3-oxooct-1-enyl)-3-(2-tetrahydropyranyloxy)cyclopentyl]heptanoic acid [prepared as described above in Example 4(b)] for the 7-[2-oxo-5-(3-oxooct-1-enyl)-3-(2-tetrahydropyranyloxy)cyclopentyl]heptanoic acid used as starting material, there was prepared 7-[2-hydroxy-5-(3-hydroxy-4-methyloct-1-enyl)-3-(2-tetrahydropyranyloxy)cyclopentyl]heptanoic acid.

d. Preparation of 7-[2,3-dihydroxy-5-(3-hydroxy-4-methyloct-1-enyl)cyclopentyl]heptanoic acid A mixture of 7-[2-hydroxy-5-(3-hydroxy-4-methyloct-1-3-(2-tetrahydropyranyloxy)cyclopentyl]-heptanoic acid (1.06 g.), glacial acetic acid (40 ml.) and water (20 ml.) was stirred at 40°C. for 4 hours. The mixture was then treated with water (50 ml.) and extracted with diethyl ether (2 × 50 ml.). The combined ethereal extracts were washed once with water, dried over magnesium sulphate, and concentrated in vacuo to low volume. Repeatedly, small portions of benzene were then added, concentrating in vacuo in order to remove last traces of acetic acid, and then the mixture was evaporated to dryness. The residue (0.5 g.) was subjected to preparative thin-layer chromatography on silica gel, using a mixture of ethyl acetate, cyclohexane and formic acid (40:40:1 by volume) as the eluent, to give 7-[2,3-dihydroxy-5-(3-hydroxy-4-methyloct-1-enyl)cyclopentyl]heptanoic acid (0.045 g.), $\nu_{max}$ 1705 cm$^{-1}$, 980 cm$^{-1}$.

EXAMPLE 5

Preparation of
7-[3-hydroxy-2-oxo-5-(3-oxooct-1-enyl)cyclopentyl]-heptanoic acid By proceeding in a manner similar to that hereinbefore described in Example 4(d) for the preparation of 7-[2,3-dihydroxy-5-(3-hydroxy-4-methyloct-1-enyl)cyclopentyl]heptanoic acid, but substituting 7-[2-oxo-5-(3-oxooct-1-enyl)-3-(2-tetrahydropyranyloxy)cyclopentyl]heptanoic acid [prepared as hereinbefore described in Example 2(g)] for the 7-[2-hydroxy-5-(3-hydroxy-4-methyloct-1-3-(2-tetrahydropyranyloxy)cyclopentyl]heptanoic acid used as starting material, there was prepared 7-[3-hydroxy-2-oxo-5-(3-oxooct-1-enyl)cyclopentyl]heptanoic acid, $\nu_{max}$ 3400cm$^{-1}$, 1700cm$^{-1}$, 1625cm$^{-1}$, 985cm$^{-1}$, $\lambda_{max}$ 225m$\mu$.

EXAMPLE 6

Preparation of
7-[2,3-dihydroxy-5-(3-hydroxyoct-1-enyl)cyclopentyl]heptanoic acid.

By proceeding in a manner similar to that hereinbefore described in Example 2(h) for the preparation of 7-[2-hydroxy-5-(3-hydroxyoct-1-enyl)-3-(2-tetrahydropyranyloxy)cyclopentyl]heptanoic acid, but substituting 7-[3-hydroxy-2-oxo-5-(3-oxooct-1-enyl)cyclopentyl]heptanoic acid [prepared as hereinbefore described in Example 5] for the 7-[2-oxo-5-(3-oxooct-1-enyl)-3-(2-tetrahydropyranyloxy)cyclopentyl]heptanoic acid used as starting material, there was prepared 7-[2,3-dihydroxy-5-(3-hydroxyoct-1-enyl)cyclopentyl]heptanoic acid, $\nu_{max}$1700cm$^{-1}$, 980cm$^{-1}$.

The present invention includes within its scope pharmaceutical compositions which comprise at least one compound of the above-mentioned novel class of cyclopentane derivatives of general formula I or, when R$^1$ represents a hydrogen atom, a non-toxic salt thereof, together with a pharmaceutical carrier or coating. In clinical practice the novel compounds of the present invention will normally be administered orally, rectally, vaginally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, or lactose. The compositions may also comprise, as is normal practice, additional substances other than inert diluents, e.g., lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions, by irradiation, or by heating. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment. In the adult, the doses are generally between 0.02 and 2.0 mg. by aerosol administration as bronchodilators, between 0.0002 and 2.0 mg./kg. body weight by intravenous administration, preferably by intravenous infusion at a rate of between 0.0001 and 1.0 mg./kg. body weight/minute as hypotensives, between 0.001 and 0.3 mg./kg. body weight orally as inhibitors of gastric acid secretion and between 0.01 and 1.0 mg./kg. body weight by intravenous administration, preferably by intravenous infusion at a rate of between 0.02 and 20 $\mu$g./kg. body weight/minute as stimulators of uterine contraction. If necessary these doses may be repeated as and when required.

The compounds of general formula I and, when R$^1$ represents a hydrogen atom, non-toxic salts thereof may be administered orally as bronchodilators by any method known per se for administration by inhalation of drugs which are not themselves gaseous under normal conditions of administration. Thus, a solution of the active ingredient in a suitable pharmaceutically-acceptable solvent, for example water, can be nebulized by a mechanical nebulizer, for example a Wright Nebulizer, to give an aerosol of finely-divided liquid particles suitable for inhalation. Advantageously, the solution to be nebulized is diluted, and aqueous solutions containing from 0.02 to 20 mg., and preferably 0.2 to 5.0 mg., of active ingredient per ml. of solution are particularly suitable. The solution may contain stabilizing agents such as sodium bisulphite and buffering agents to give it an isotonic character, e.g., sodium chloride, sodium citrate and citric acid.

The active ingredients may also be administered orally by inhalation in the form of aerosols generated from self-propelling pharmaceutical compositions. Compositions suitable for this purpose may be obtained by dissolving or suspending in finely-divided form, preferably micronized to an average particle size of less than 5 microns, the active ingredients in pharmaceutically-acceptable solvents, e.g., ethanol, which are co-solvents assisting in dissolving the active ingredients in the volatile liquid propellants hereinafter described, or pharmaceutically-acceptable suspending or dispersing agents, for example aliphatic alcohols such as oleyl alcohol, and incorporating the solutions or suspensions obtained with pharmaceutically-acceptable volatile liquid propellants, in conventional pressurized packs which may be made of any suitable material, e.g., metal, plastics or glass, adequate to withstand the pressures generated by the volatile propellant in the pack. Pressurized pharmaceutically-acceptable gases, such as nitrogen, may also be used as propellants. The pressurized pack is preferably fitted with a metered valve which dispenses a controlled quantity of the self-propelling aerosol composition as a single dose.

Suitable volatile liquid propellants are known in the art and include fluorochlorinated alkanes containing from one to four, and preferably one or two, carbon atoms, for example dichlorodifluoromethane, dichlorotetrafluoroethane, trichloromonofluoromethane, dichloromonofluoromethane and monochlorotrifluoromethane. Preferably, the vapour pressure of the volatile liquid propellant is between about 25 and 65 pounds, and more especially between about 30 and 55 pounds, per square inch gauge at 21°C. As is well-known in the art, volatile liquid propellants of different vapour pressures may be mixed in varying proportions to give a propellant having a vapour pressure appropriate to the production of a satisfactory aerosol and suitable for the chosen container. For example dichlorodifluoromethane (vapour pressure 85 pounds per square inch gauge at 21°C.) and dichlorotetrafluoroethane (vapour pressure 28 pounds per square inch gauge at 21°C.) may be mixed in varying proportions to give propellants having vapour pressures intermediate between those of two constituents, e.g., a mixture of dichlorodifluoromethane and dichlorotetrafluoroethane in the proportions 38:62 respectively by weight has a vapour pressure of 53 pounds per square inch gauge at 21°C.

The self-propelling pharmaceutical compositions may be prepared by dissolving the required quantity of active ingredient in the co-solvent or combining the required quantity of active ingredient with a measured quantity of suspending or dispersing agent. A measured quantity of this composition is then placed in an open container which is to be used as the pressurized pack. The container and its contents are then cooled below the boiling temperature of the volatile propellant to be used. The required quantity of liquid propellant, cooled below its boiling temperature, is then added and the contents of the container mixed. The container is then sealed with the required valve fitting, without allowing the temperature to rise above the boiling temperature of the propellant. The temperature of the sealed container is then allowed to rise to ambient with shaking to ensure complete homogeneity of the contents to give a pressurized pack suitable for generating aerosols for inhalation. Alternatively, the co-solvent solution of the active ingredient or combination of active ingredient and suspending or dispersing agent is placed in the open container, the container sealed with a valve, and the liquid propellant introduced under pressure.

Means for producing self-propelling compositions for generating aerosols for the administration of medicaments are, for example, described in detail in U.S. Pat. Nos. 2,868,691 and 3,095,355.

Preferably, the self-propelling pharmaceutical compositions according to the present invention contain from 0.2 to 20 mg., and more particularly 0.2 to 5.0 mg., of active ingredient per ml. of solution or suspension. It is important that the pH of solutions and suspensions used, according to the present invention, to generate aerosols should be kept within the range 3 to 8 and preferable that they should be stored at or below 4°C., to avoid pharmacological deactivation of the active ingredient.

In carrying out the present invention, the means of producing an aerosol for inhalation should be selected in accordance with the physico-chemical properties of the active ingredient.

By the term "pharmaceutically-acceptable" as applied in this specification to solvents, suspending or dispersing agents, propellants and gases is meant solvents, suspending or dispersing agents, propellants and gases which are non-toxic when used in aerosols suitable for inhalation therapy.

It is highly desirable that the aerosols should have a particle size less than about 10 microns and preferably less than 5 microns, for example between 0.5 and 3 microns, to ensure effective distribution to very narrow bronchioles. Preferably, administration is by means of devices enabling controlled quantities of the active ingredients to be administered, for example by means of the metered valves hereinbefore mentioned.

The following Example illustrates pharmaceutical compositions according to the invention.

EXAMPLE 7

7-[3,4-Dihydroxy-2-(3-hydroxyoctyl)cyclopentyl]-heptanoic acid (300 mg.) was dissolved in ethanol (1 ml.) and the solution obtained was added to an aqueous solution (12 ml.) containing sodium carbonate (50 mg.). Aqueous sodium chloride solution (0.9% w/v, 2 ml.) was then added to give a final volume of 15 ml. The solution was then sterilized by passage through a bacteria-retaining filter and placed in 1.5 ml. portions in 5 ml. ampoules, to give 30 mg. of the heptanoic acid derivative (in the form of its sodium salt) per ampoule. The contents of the ampoules were freeze-dried and the ampoules sealed. The contents of an ampoule in a suitable volume, e.g. 2 ml., of sterile water or physiological saline gave a solution ready for administration by injection.

We claim:

1. A cyclopentane of the formula:

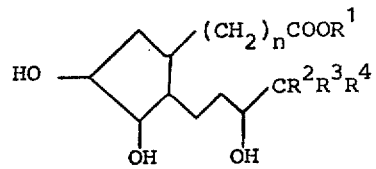

wherein $R^1$ represents hydrogen or alkyl of 1 through 12 carbon atoms, $R^2$ and $R^3$ represent hydrogen or alkyl of 1 through 4 carbon atoms, $R^4$ represents alkyl of 1 through 10 carbon atoms, and $n$ represents 4 or 6, and, where $R^1$ represents hydrogen, non-toxic salts thereof.

2. A cyclopentane according to claim 1 wherein $R^1$ represents hydrogen or alkyl of 1 through 4 carbon atoms, $R^2$, $R^3$ and $R^4$ are as defined in claim 1, and $n$ represents 6.

3. A cyclopentane according to claim 1 wherein $R^4$ represents alkyl of 2 through 9 carbon atoms.

4. A cyclopentane according to claim 1 wherein $R^4$ represents alkyl of 3, 4, or 6 carbon atoms.

5. A cyclopentane according to claim 1 wherein $R^1$ represents hydrogen, methyl or ethyl.

6. A cyclopentane according to claim 1 wherein $R^2$ represents hydrogen, $R^3$ represents hydrogen or methyl, and $R^4$ represents propyl, butyl or hexyl.

7. An alkyl ester of an acid claimed in claim 1 in which the alkyl ester group contains 1 through 4 or 7 through 12 carbon atoms.

8. The cyclopentane derivative according to claim 1 which is 7-[3,4-dihydroxy-2-(3-hydroxyoctyl)-cyclopentyl]heptanoic acid and non-toxic salts and alkyl esters thereof in which the alkyl ester group contains 1 through 12 carbon atoms.

9. An alkyl ester of the acid claimed in claim 8 in which the alkyl ester group contains 1 through 4 or 7 through 12 carbon atoms.

10. The methyl and ethyl esters and sodium salt of the acid claimed in claim 8.

* * * * *